(12) United States Patent
Hladky (10) Patent No.: US 7,241,261 B2
(45) Date of Patent: Jul. 10, 2007

(54) DUAL USE SYRINGE

(75) Inventor: Donald F. Hladky, Janesville, WI (US)

(73) Assignee: Continental Plastic Corp., Delavan, WI (US)

( * ) Notice: Subject to any disclaimer, the term of this patent is extended or adjusted under 35 U.S.C. 154(b) by 603 days.

(21) Appl. No.: 10/143,615

(22) Filed: May 10, 2002

(65) Prior Publication Data

US 2003/0212307 A1   Nov. 13, 2003

(51) Int. Cl.
*A61D 7/00* (2006.01)
(52) U.S. Cl. .......................................... 600/35; 600/33
(58) Field of Classification Search ................ 604/57, 604/59, 60, 61, 218, 232, 906, 264, 187; 600/33–35
See application file for complete search history.

(56) References Cited

U.S. PATENT DOCUMENTS

| | | | |
|---|---|---|---|
| 3,160,156 A | | 12/1964 | Tyler |
| 3,507,281 A | * | 4/1970 | Cassou ...................... 604/232 |
| 3,744,493 A | * | 7/1973 | Booher et al. ................ 604/62 |
| 3,910,275 A | | 10/1975 | Babey et al. |
| 4,006,849 A | | 2/1977 | van Vroenhoven |
| 4,173,227 A | | 11/1979 | Cassou et al. |
| 4,261,361 A | | 4/1981 | Cassou |
| 4,453,936 A | | 6/1984 | Cassou |
| 4,478,261 A | | 10/1984 | Cassou et al. |
| 4,493,700 A | * | 1/1985 | Cassou et al. ................ 600/35 |
| 4,846,785 A | | 7/1989 | Cassou et al. |
| 4,865,589 A | | 9/1989 | Simmet et al. |
| 4,900,304 A | * | 2/1990 | Fujioka et al. ................ 604/60 |
| 4,994,028 A | * | 2/1991 | Leonard et al. ............... 604/60 |
| 5,190,880 A | | 3/1993 | Cassou et al. |
| 5,405,326 A | * | 4/1995 | Haber et al. ................. 604/110 |
| 5,496,272 A | * | 3/1996 | Chung et al. ................ 604/515 |
| 5,849,022 A | * | 12/1998 | Sakashita et al. ........... 606/174 |
| 6,478,780 B1 | * | 11/2002 | Shields ........................ 604/263 |
| 2002/0087175 A1 | * | 7/2002 | Gifford et al. .............. 606/153 |

FOREIGN PATENT DOCUMENTS

| | | |
|---|---|---|
| DE | 43 09 808 C | 6/1994 |
| DE | 43 09 808 C1 | 6/1994 |
| EP | 1 066 802 A | 1/2001 |
| GB | 867 274 A | 5/1961 |

* cited by examiner

*Primary Examiner*—Kevin C. Sirmons
*Assistant Examiner*—Catherine N. Witczak
(74) *Attorney, Agent, or Firm*—Boyle Fredrickson Newholm Stein & Gratz S.C.

(57) ABSTRACT

An injection syringe for the injection of materials into domestic animals is provided. The syringe includes a tubular body having a guide member positioned within the body that is adapted to engage and properly position fluid containing straws of varying diameters with respect to the syringe. A plunger can be inserted through the body and through the guide member to expel the material from within the straw out of the body. The tubular body and the straws that can be used with the tube can be positioned within a conventional, removable hygienic sheath, that allows the syringe to be used for numerous fluid transfers.

22 Claims, 7 Drawing Sheets

DUAL USE SYRINGE

FIELD OF THE INVENTION

The present invention relates to injection devices, and more specifically to syringes or guns used to penetrate a uterus to transfer medicines, artificially inseminate animals, or transfer embryos.

BACKGROUND OF THE INVENTION

In order to artificially impregnate domestic animals, a number of devices have been designed. The most well recognized and utilized device that has been developed is an artificial insemination syringe or gun. While the words syringe and gun are often used interchangeably in the industry and within this application, the word syringe is believed to be technically broader in scope.

A number of different configurations for guns or syringes of this type have been developed, such as those disclosed in U.S. Pat. Nos. 4,173,227, 4,261,361, 4,846,785 and 4,865,589, which are hereby incorporated by reference in their entirety. The syringe comprises a tubular body adapted to receive a container holding the biological material to be injected into the animal. The body and container can be inserted into the animal and the material is expelled from the container by a push-rod or plunger slidably insertable into the body and the container. To enable the syringe to be used repeatedly without becoming contaminated by a particular animal, a flexible sheath can be removably positioned around the body to prevent contact of the internal fluids of the animal with the body of the gun, allowing the syringe to be reused a number of times. After each use, the sheath can be removed from around the body of the syringe and discarded, allowing a new, sterile sheath to be placed around the syringe.

When injecting material from this type of syringe in order to, for example, artificially inseminate a domestic animal, the material is normally contained within a plastic straw, such as that disclosed in U.S. Pat. Nos. 4,478,261 and 5,190,880 which are incorporated by reference herein. The straw is generally a plastic tubular structure that is sealed at one end by a pair of plugs and sealed at the other end with ultrasound. These seals retain the material within the straw. To use the straw, the ultrasound sealed end is first severed from the remainder of the straw. The end of the straw containing the plug pair is then inserted into and engaged by the body of the syringe. The straw is held in this position by the sheath placed around the body. When properly positioned, the plunger is inserted into the body and into the straw such that the plug is contacted and urged along the length of straw by the plunger to expel the material from within the straw out the opposite end.

The straws come mainly in two sizes, a smaller diameter straw having a volume of approximately one quarter cubic centimeter (¼ cc), and a larger diameter straw having a volume of approximately one half cubic centimeter (½ cc). Thus, in order to effectively discharge the material from within a particular diameter straw, the gun or syringe must be compatible with the diameter of the straw in which the material is contained. Thus, due to the different sizes of the straws available, on many occasions it is necessary for an individual conducting such procedures to change the type of syringe being used in order to accommodate the size of the straw containing the biological material to be injected. This is undesirable as it is inconvenient to constantly switch between syringes when utilizing straws of different sizes. Furthermore, based on the small differences in the sizes of the different types of straws and between the configuration of the various syringes, it may often be the case that an individual inadvertently uses a syringe with a straw that is not compatible with the syringe, thereby wasting the valuable biological material contained within the straw.

Therefore, to overcome this deficiency, an injecting syringe was developed that was capable of accommodating straws of multiple sizes. This syringe is disclosed in U.S. Pat. No. 4,173,227 and includes a tubular body defining an internal, axial cavity separated into two halves having a different diameters by a tubular insert positioned within the body. Each half is capable of receiving and retaining a straw having a specific diameter, such that the injecting syringe can utilize the straws having each of these diameters.

However, to change the configuration of this syringe to accommodate a straw having one of the two compatible diameters, the syringe must be partially disassembled in order to reverse the configuration of the body, thereby switching the ejection or outlet end of the body from one end to the other. By having to disassemble and reverse the configuration of the syringe, it is often the case that leaks occur between the reassembled elements of the syringe, such that some or all of the biological material that was to be injected is lost before it can be used. Moreover, having to repeatedly turn the syringe around is a nuisance when in a hurry.

Therefore, it is desirable to develop an injecting syringe that is capable of accommodating straws having different diameters that does not require disassembling and/or altering the syringe to prevent the material from leaking out of the syringe.

SUMMARY OF THE INVENTION

It is an object of the present invention to provide an injecting syringe for use in artificially inseminating animals with a biological material that can be used with straws of differing diameters.

It is another object of the invention to provide an injecting syringe which has a one-piece body that prevents leakage of any material from within the syringe.

It is a further object of the invention to provide an injecting syringe having a design similar to prior art injecting syringes to allow the syringe to be used with pre-existing syringe components, including sheaths, straw-retaining sheath inserts and straws.

It is still another object of the invention to provide an injecting syringe that has a simple and inexpensive construction.

One preferred embodiment of the present invention is an injecting gun or syringe for artificially impregnating domestic animals that enables biological material-containing straws of different diameters to be utilized with the syringe. The injecting syringe includes a tubular body that defines an axial passage extending therethrough and includes a head fixedly attached at one end. The tubular body includes a guide member disposed within the passage that serves to properly position and retain the straws inserted into the passage opposite the head. The guide member includes a stop that engages straws having a larger diameter. The stop encircles a recess that is dimensioned to receive and retain straws contacting the guide member that have a smaller diameter. The syringe also includes a push rod or plunger that is removably insertable through the head, the tubular body and the guide member into the straw to expel the biological material contained within the straw outwardly from the syringe. The body can also be releasably positioned within a protective sheath, which prevents the syringe from contacting any fluids of the animals with which the syringe is used. This allows the syringe to be used repeatedly on a large number of different animals without spreading any disease or other medical conditions between the animals.

Alternatively, the invention may be a gun assembly used to inject a material into an animal with a tubular body. The tubular body has a first end and a second end, an axial passage extending therethrough, and a guide member fixedly positioned within the axial passage of the body. The guide member has a stop engageable with a large diameter straw when inserted into the axial passage in the body through the second end, a recess extending into the guide member adjacent the stop and engageable with a small diameter straw when inserted into the passage in the body through the second end, and an axial throughbore intersecting the recess.

The stop of the syringe may be formed by an increase in the interior thickness of the guide member from the throughbore to the one end. Further, the recess may have a bore with a continuously decreasing diameter in order to prevent the straw from moving upon insertion of the plunger. The recess may also have a frustoconical surface with a gradually increasing thickness from the throughbore to the one end for preventing the straw from moving.

The invention further includes a method for artificially insemination providing a syringe assembly with a tubular body having a head with an axial aperture fixedly attached at one end and an open end opposite the head. The body may define an axial passage therethrough with a guide member fixed within the axial passage and spaced from the head. The guide member preferably includes a stop located opposite the head, a recess extending inwardly into the guide member from the stop, and an axial throughbore communicating with the recess. A plunger is also included with an elongate rod having a handle at one end. The rod is dimensioned to be insertable through the aperture in the head, the passage in the tubular body, and the throughbore in the guide member. The elongate straw contains an amount of a biological material and has a plug formed of a deformable material adjacent one end and an open end opposite the plug. When in use, the user engages the end of the straw adjacent the plug with the guide means within the body, inserts the rod through the aperture in the head into the passage within the body, and then presses the handle towards the head to urge the rod through the throughbore in the guide member and into contact with the plug in the straw to force the plug along the straw and urge the biological material out of the straw through the open end of the body.

Various other features, details and embodiments of the present invention will be made apparent from the following detailed description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

The present invention and the various features and advantageous details thereof are explained more fully with reference to the non-limiting embodiments described in detail in the following description.

1. Preferred Embodiments

Figure 1:
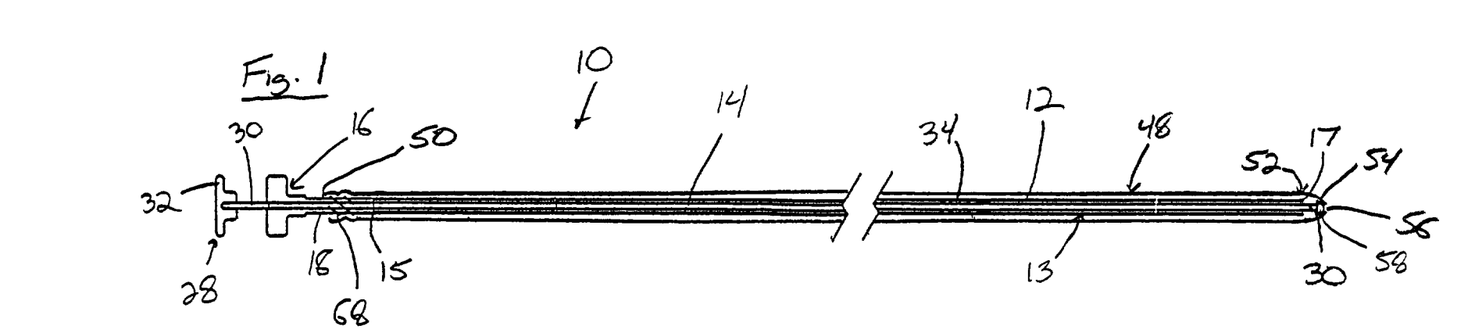
FIG. 1 is a cross-sectional view of an injecting syringe constructed according to the present invention.

With reference now to the drawing figures in which like reference numerals designate like parts throughout the disclosure, an injecting syringe or gun constructed according to the present invention is indicated generally at 10 in FIG. 1. The syringe 10 includes a barrel or tubular body 12 formed of a generally rigid material, such as a metal or a plastic, and preferably stainless steel. If bent the material is able to regain its shape without a loss in performance. The tubular body 12 defines an axial passage 14 therethrough. Furthermore, the syringe 10 can be disposable if desired.

Figure 5:
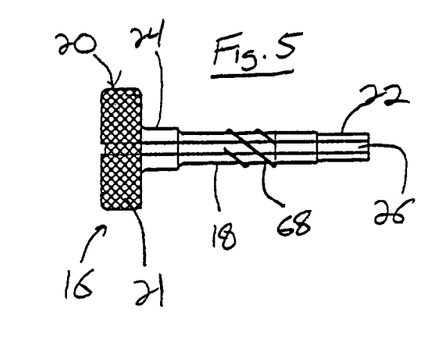
FIG. 5 is a side plan view of the head of the injecting syringe of FIG. 1.

Looking now at FIGS. 1 and 5, a first end 15 of the body 12 is attached to a head 16 formed from a material similar to that used for the body 12 and which forms a gripable portion of the syringe 10 opposite a second end 17. The head 16 includes a tubular body section or tube 18 and a circular flange section 20 that can be fixedly attached to or integrally formed with one end of the body section 18. The flange section or flange 20 has an exterior circumferential surface 21 that can be knurled, pebbled, pitted, or otherwise altered to allow the flange 20 to be gripped more easily.

Opposite the flange 20, the tube 18 preferably includes a first or reduced diameter section 22 that is insertable into the first end 15 of the tubular body 12. Because it is formed of a generally rigid material similar to that used for the body 12, the reduced diameter section 22 can be secured within the tubular body 12 by any suitable means, such as by an adhesive or by laser welding the reduced diameter section 22 to the interior of the body 12. Opposite the reduced diameter section 22, the tube 18 preferably includes a second or enlarged diameter section 24 extending between the tube 18 and the flange 20. The head 16 also preferably defines an axial passage 26 that extends completely through the head 16 from the flange 20 to the reduced diameter section 22 and is aligned with the passage 14 extending through the tubular body 12.

In one embodiment, the tubular body 12 may be constructed of several tubes of smaller lengths with varying flexibility/rigidity.

The syringe 10 also preferably includes a push rod or plunger 28 including an elongate rod 30 and a circular knob or handle 32 attached to one end of the rod 30 by any suitable means, such as by an adhesive or by welding. Alternatively, the handle 32 can be integrally formed with the rod 30 (see, e.g., FIG. 11). The rod 30 has a diameter less than the diameter of the passage 26 in the head 16 and the passage 14 in the body 12, such that the rod 30 can be slid into and pass through the head 16 and the tubular body 12. The rod 30 and handle 32 are formed of a generally rigid material similar to the body 12. Also, the rod 30 has an overall length slightly greater than the combined length of the head 16 and tubular body 12, such that the rod 30 can project outwardly from the body 12 when the handle 32 of the plunger 28 is pressed against the head 16.

Figure 11:
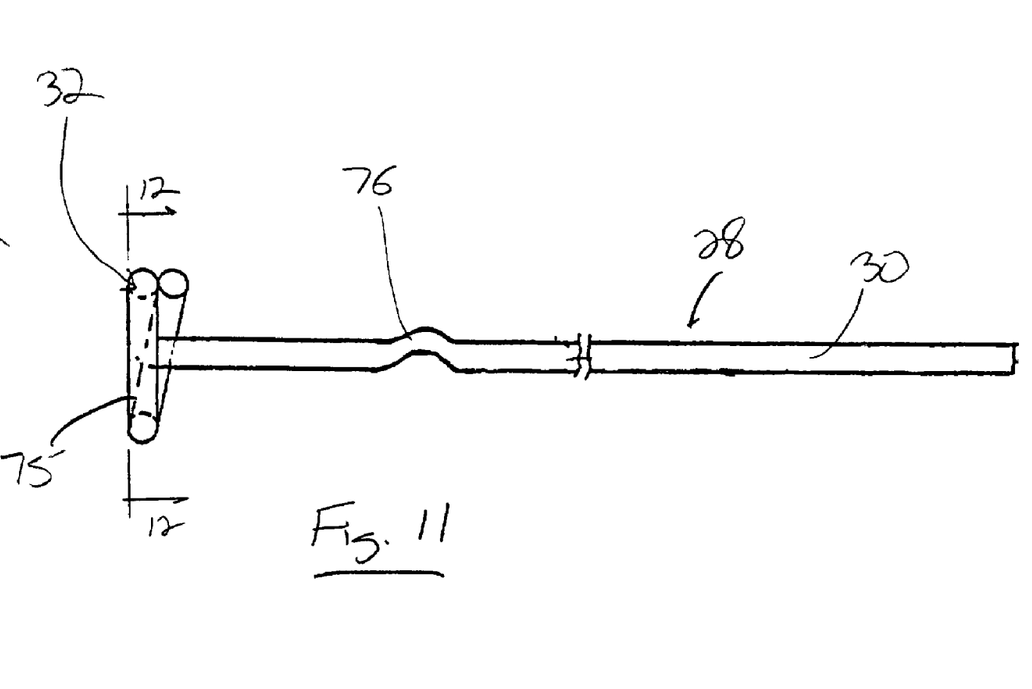
FIG. 11 is a second embodiment of a plunger used with the syringe of FIG. 10.
Figure 12:
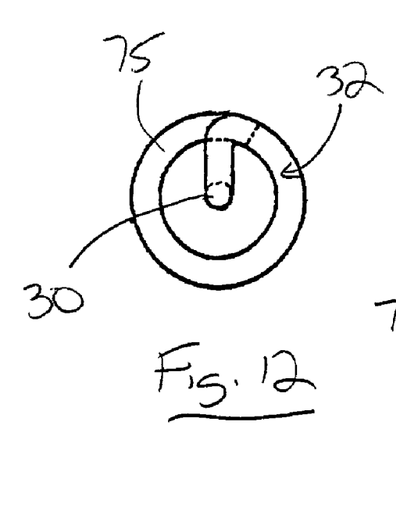
FIG. 12 is a cross-sectional view along line 12—12 of FIG. 11.

Referring now to FIGS. 11 and 12, the plunger 28 can also be formed from a single, unitary rod 30. The rod 30 is bent and spirally wound at one end in order to form an integrally connected loop 75 that functions as the handle 32. The formation of the plunger 28 in this manner greatly reduces the overall cost and complexity of assembling the plunger 28, as the plunger 28 includes only one part, negating any assembly of a separate handle 32 and rod 30. Further, in order to enable the plunger 28 to be held within the body 12 when the syringe 10 is positioned vertically (with the handle below a guide member 34) to insert a straw 36, the plunger 28 can include a bend, marker or kink 76 at a specified point along the rod 30. The bend 76 slides along the interior wall of the body 12 and prevents the plunger 28 from inadvertently sliding entirely out of the body 12 by contacting the end of the tube 18. However, the bend 76 is conveniently positioned far enough from the tip of the rod 30 opposite the handle 32 such that the bend 76 does not interfere with the operation of the plunger 28 as it is pushed through the body 12. Preferably the bend 76 is spaced from the handle 32 a distance slightly longer than the length of a straw 36, and most preferably about six (6) inches from the handle 32.

In order that the bend 76 can flex sufficiently in order to allow the plunger 28 to be utilized correctly and removed from the syringe 10 when necessary, the rod 30 is formed from a somewhat resilient, but generally rigid material, such as a hard plastic or preferably a spring-tempered stainless steel.

Figure 13:
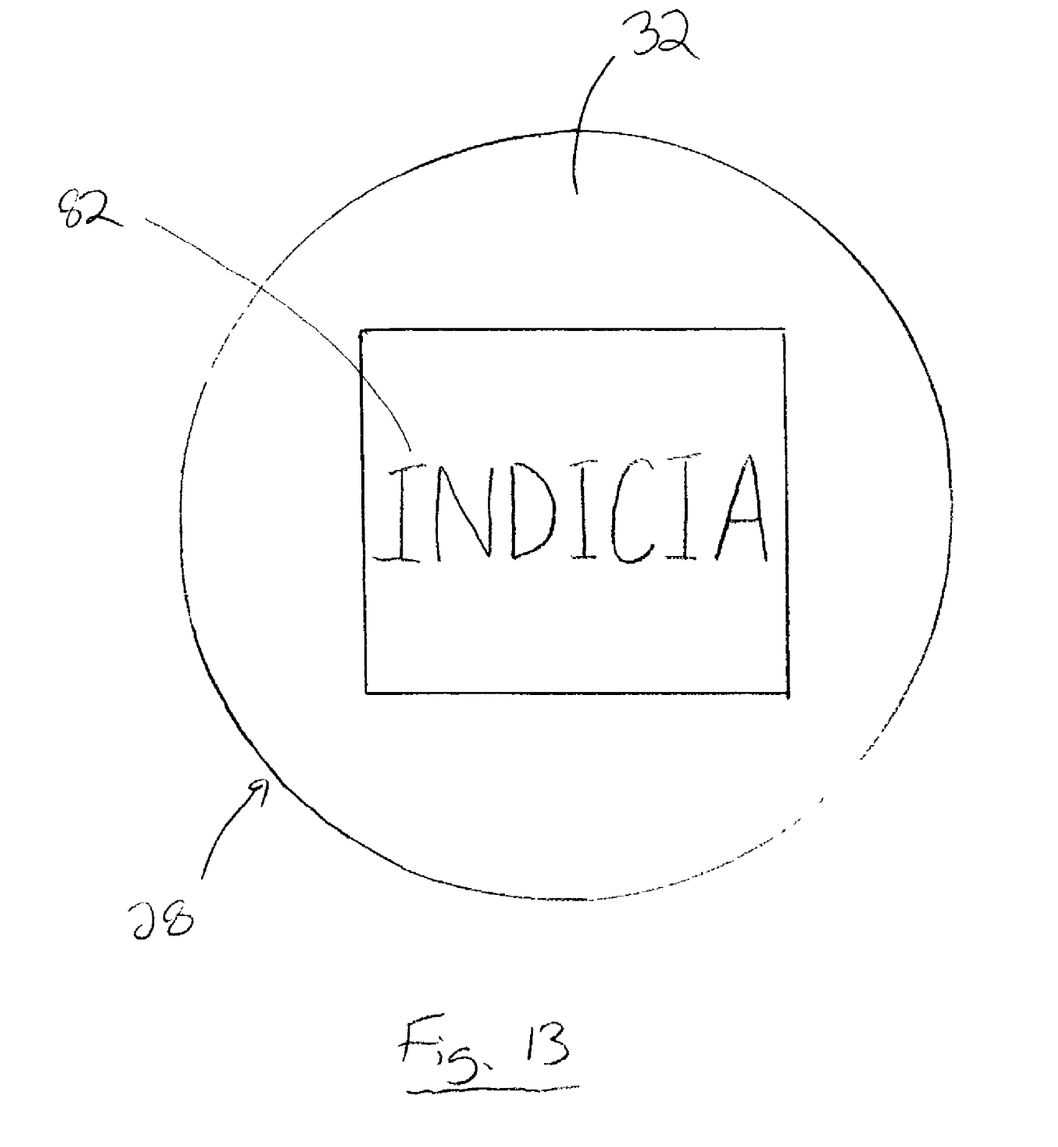
FIG. 13 is a top plan view of the plunger of FIG. 1 including laser-etched indicia on the plunger.

To enhance the identification of different syringes 10, as best shown in FIG. 13, the plunger 28 can also have identifying indicia 82 etched on the handle 32 of the plunger 28 opposite the rod 30. The indicia 82 can be laser mark printed or etched onto the handle 32, and can indicate the owner of the syringe 10, the breed or type of livestock, or the manufacturer of the syringe 10 among other types of information. Alternatively or in addition, the indicia 82 can be etched onto the exterior of the tubular body 12, if desired.

Figure 10:
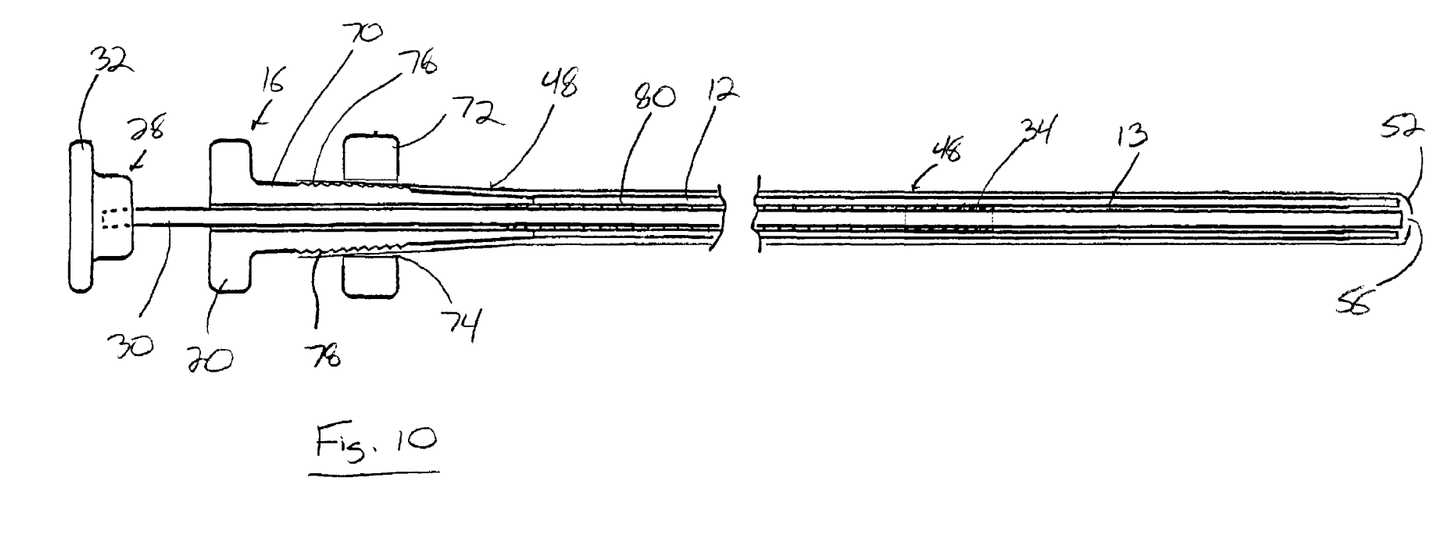
FIG. 10 is a third embodiment of the syringe of FIG. 2.

Referring now to FIGS. 1–4, the tubular body 12 also includes an inner guide member 34 fixedly disposed within the passage 14 and spaced from the head 16 and forming a straw chamber 13 between the guide member 34 and the second end 17 of the body 12. The guide member 34 is formed of a rigid material, such as hard plastic or metal, with a stainless steel similar to the body 12 being preferred, and is generally cylindrical in shape, defining a passage such as a throughbore 35 therethrough. However, the guide member 34 can have a cross-section other than circular, such as square, hexagonal or octagonal, for example, so long as the guide member 34 can fixedly contact the interior of the body 12 and is secured in position by welding or otherwise securing the guide member 34 within the body 12. Preferably, the guide member 34 has an exterior diameter slightly less than the diameter of the passage 14 through the tubular body 12 and an interior passage diameter slightly larger than the diameter of the rod 30. The guide member 34 is positioned within the body 12 between the center of the tubular body 12 and the second end 17 of the body 12 in order to form or define the straw chamber 13 between the guide member 34 and the second end 17. Preferably, the guide member 34 is positioned within the body 12 such that the guide member 34 is spaced from the second end 17 of the tubular body 12 a distance slightly less than the overall length of a straw 36 containing to biological material to be injected by the syringe 10. In order to ensure the proper positioning of the guide member 34 within the body 12, the body 12 may also include a spacing member 80, best shown in FIG. 10, which abuts the guide member 34 opposite the straw chamber 13 in order to ensure that the straw chamber 13 has the desired size, i.e., approximately equal to the length of the straw 36. As best shown in FIG. 10, member 80 abuts the guide member 34 opposite the straw chamber 13. The member 80 primarily serves to reinforce tube 12.

Figure 2:
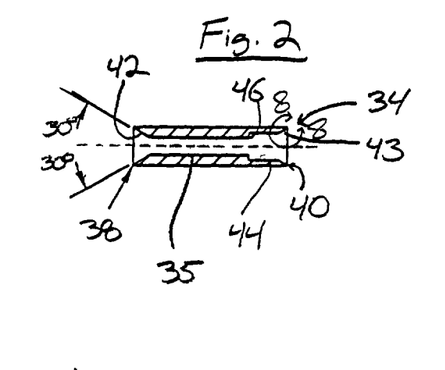
FIG. 2 is a cross-sectional view of an inner guide member positioned within the injecting syringe of FIG. 1.
Figure 3:
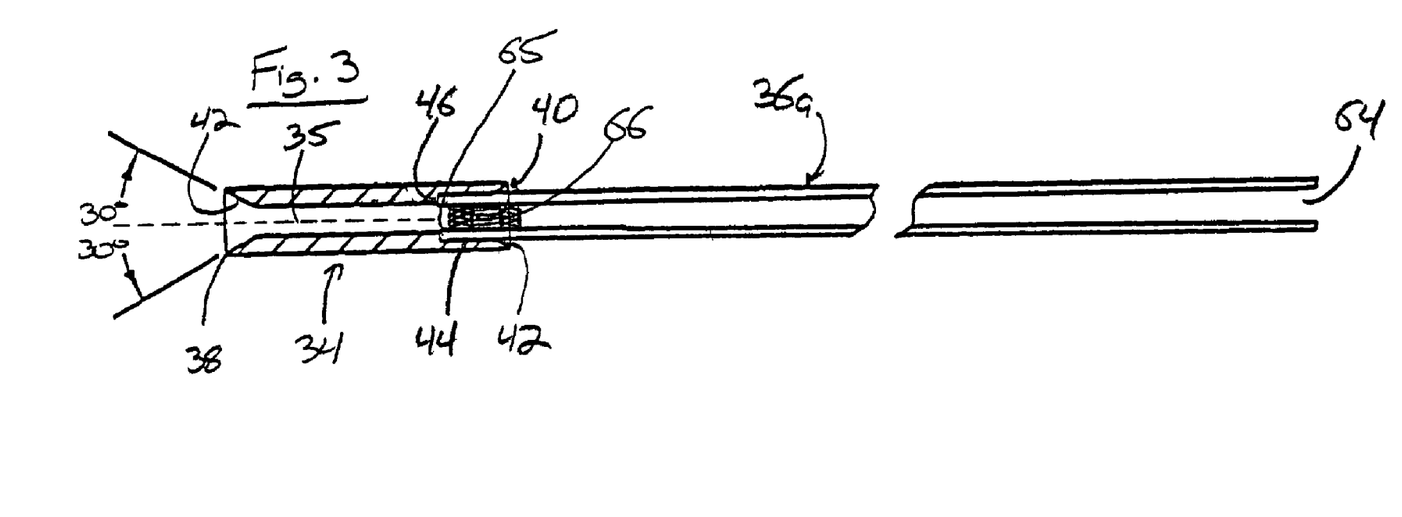
FIG. 3 is a cross-sectional view of a small diameter straw engaged with the inner guide member of FIG. 2.
Figure 4:
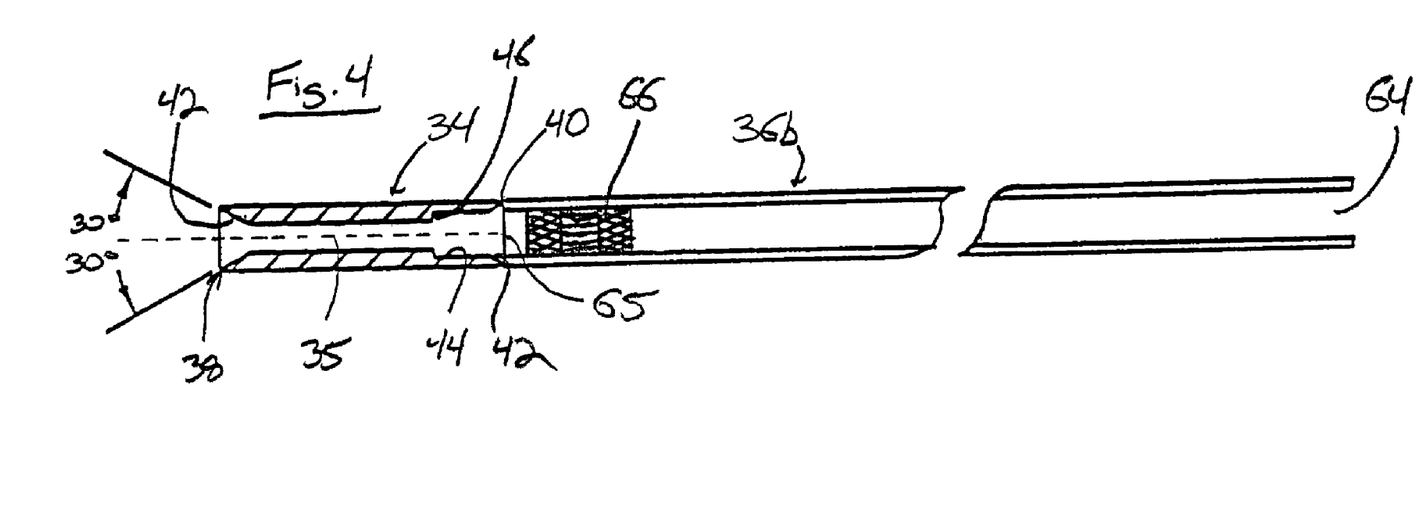
FIG. 4 is a cross-sectional view of a large diameter straw engaged with the inner guide member of FIG. 2.

As best shown in FIGS. 2–4, the guide member 34 includes a guide end 38 facing to head 16 and a stop or engagement end 40 facing the second end 17. The guide end 38 is formed of guide surface such as an outwardly tapering end section 42 of passage 35 that extends radially outwardly at an angle from the central axis of the guide member 34, which is preferably around 30°. The tapered end section 42 serves to contact and guide a second end of the rod 30 (i.e. the end opposite the handle 32) into and through the passage 35 within the guide member 34.

Figure 8:
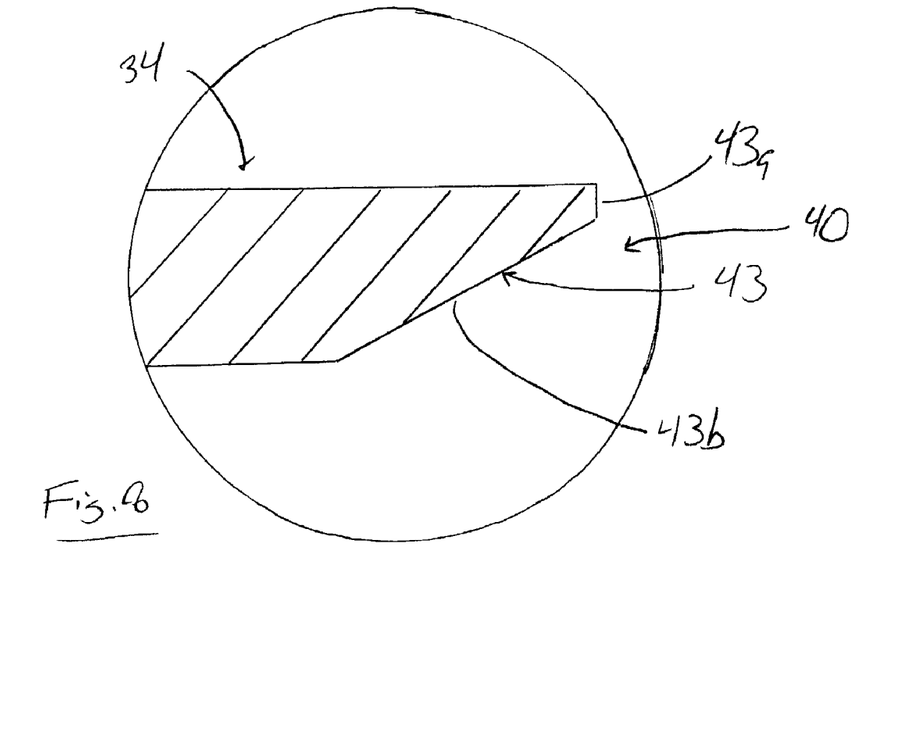
FIG. 8 is a partial sectional view along line 8—8 of FIG. 2.
Figure 9:
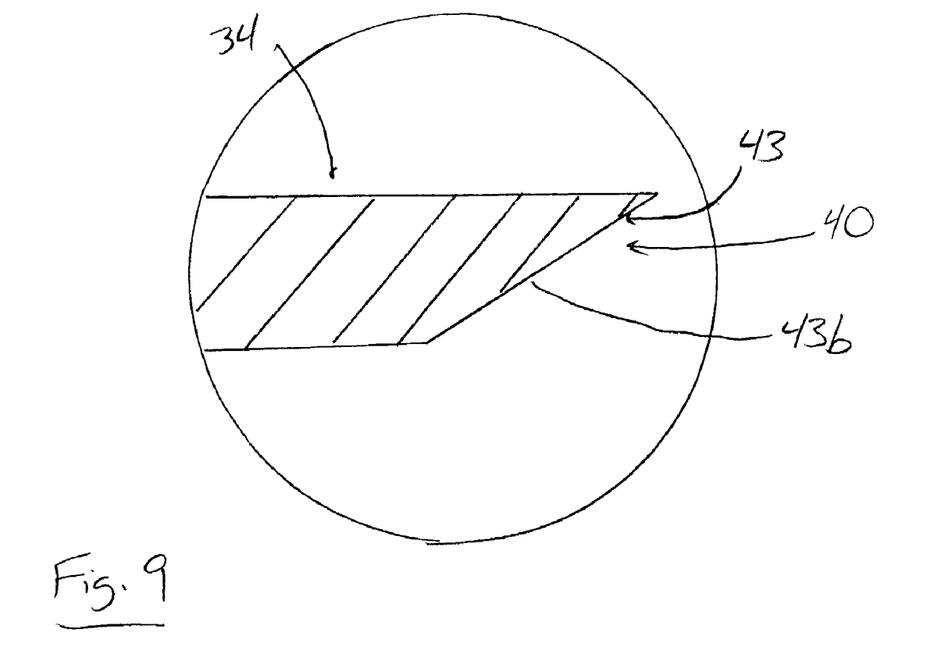
FIG. 9 is a second embodiment of the guide member shown in FIG. 8.

Opposite the guide end 38, the stop end 40 also includes an outwardly tapering end section 43 that surrounds a generally circular recess 44. The tapering end section 43 of the stop end 40 may be formed in several ways as shown in FIGS. 8 and 9. In FIG. 8, the tapering end section 43 includes a flat end portion 43a extending between the exterior of the guide member 34 and the frustoconical sloping surface 43b. Alternatively, as shown in FIG. 9, the tapering end section 43 can omit the flat end portion 43a and can comprise only the frustoconical sloping surface 43b that continuously extends between the exterior and interior of the guide member 34. The recess 44 extends inwardly from the stop end 40 to an annular shoulder 46 disposed within the interior of the inner guide 34 and formed around the passage 35. The recess 44 has a diameter approximately equal to the outer diameter of a small diameter straw 36a such that one end of the straw 36a can contact the tapered end 43 and be inserted into the recess 44 as shown in FIG. 3. Alternatively, looking now at FIG. 4, if a large diameter straw 36b is utilized with the syringe 10, the diameter of the stop end 40 is approximately equal to the outer diameter of the straw 36b, such that the straw 36b contacts the stop end 40 without entering the circular recess 44. Thus, with the guide member 34 positioned within the tubular body 12, it is possible for the syringe 10 to properly position either a small diameter straw 36a or a large diameter straw 36b in the straw chamber 13. Straw sizes typically range from ½ cc to ¼ cc.

Figure 6:
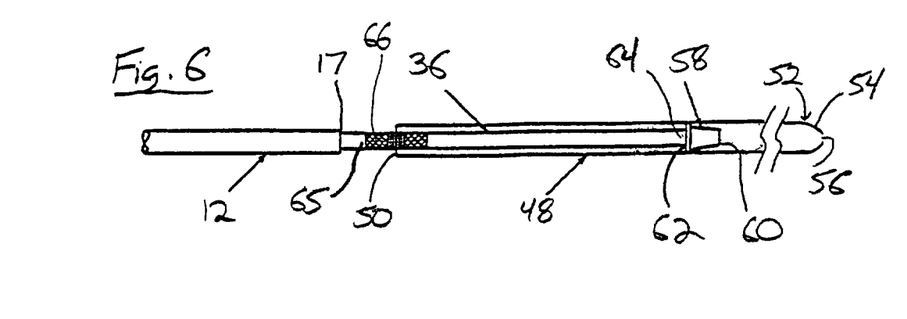
FIG. 6 is a partially broken away view of a sheath positioned around the syringe of FIG. 1.

Referring now to FIG. 6, to enable the syringe 10 to be repeatedly used for a large number of injections, the tubular body 12 of the syringe 10 is covered by a disposable tubular sheath 48. The sheath 48 is of the type disclosed in U.S. Pat. No. 4,173,277, incorporated herein by reference, and is formed of a soft, flexible material, such as a flexible plastic, with a mounting end 50 disposed opposite an injection end 52. The mounting end 50 is simply an unobstructed, open end of the tubular sheath 48 into which the tubular body 12 can be inserted. The injection end 52 includes a rounded tapering surface 54 that extends inwardly towards the center axis of the sheath 48 in order to define a restricted diameter opening 56. The restricted opening 56 has a diameter less than that of the tubular body 12, the straw 36 and the rod 30, such that only the biological material contained within the straw 36 can pass through the opening 56.

As best shown in FIG. 6, the sheath 48 also includes an insert 58 positioned within the sheath 48 and opposite the mounting end 50. The insert 58 is preferably formed of a semi-rigid material, such as a hard plastic, and is shaped in the form of an inwardly tapering conical cylinder with a wide end 62 positioned near the mounting end 50, and a narrow end 60 disposed opposite the wide end 62 and facing the injection or restricted end 52. The insert 58 is configured to receive an open end of the straw 36, of whatever size, in order to frictionally engage and secure the straw 36 within the sheath 48. While the insert or straw engaging member 58 is also used to form a seal and thus prevent leakage, some operators prefer not to use it.

Looking again at FIG. 6, the straw 36 is of the type shown in U.S. Pat. No. 5,190,880, previously incorporated herein by reference. The straw 36 preferably contains a material for artificially impregnating an animal such as semen or a fluid containing an embryo. Alternatively, the material could be a medicine. Initially the straw 36 is closed at one end by a pair of plugs 66 and the opposite end sealed with ultrasound. The plugs 66 are preferably formed of polyvinyl alcohol powder and two cotton wads, which retain the powder in place between the wads, to retain the biological material within the straw 36.

2. In Use and Operation

Right before use, the straw 36 is cut to form an open end 64 at the ultrasound sealed end. The straw 36 is engaged with the insert 58 by inserting the open end 64 of the straw 36 into the mounting end 50 of the sheath 48 until the open end 64 contacts the insert 58 (see FIG. 6). The straw 36 is then pushed into the insert 58 until the open end 64 is frictionally engaged within the insert 58. Alternatively, the straw 36 can be inserted into the straw chamber 13 of the tubular body 12.

The mounting end 50 of the sheath 48 is positioned around the tubular body 12. The sheath 48 is then slid upwardly along the tubular body 12 until the mounting end 50 is positioned around the head 16. This action also allows the open end 64 of the straw 36 to frictionally engage with the insert 58. While the sheath 48 is pushed upwardly around the tubular body 12, the second end 17 of the tubular body 12 surrounds the straw 36 and contacts the insert 58, urging the insert 58 and straw 36 along the sheath 48 towards the injection end 52.

For the spiral embodiment shown best in FIG. 1, a ¼ cc straw will seat nearly automatically. With the O-ring embodiment best shown in FIG. 7, after the a ¼ cc straw is loaded the straw should extend approximately ½ inches from the body. Turning the straw one-quarter turn will ensure the straw is properly seated.

Figure 7:
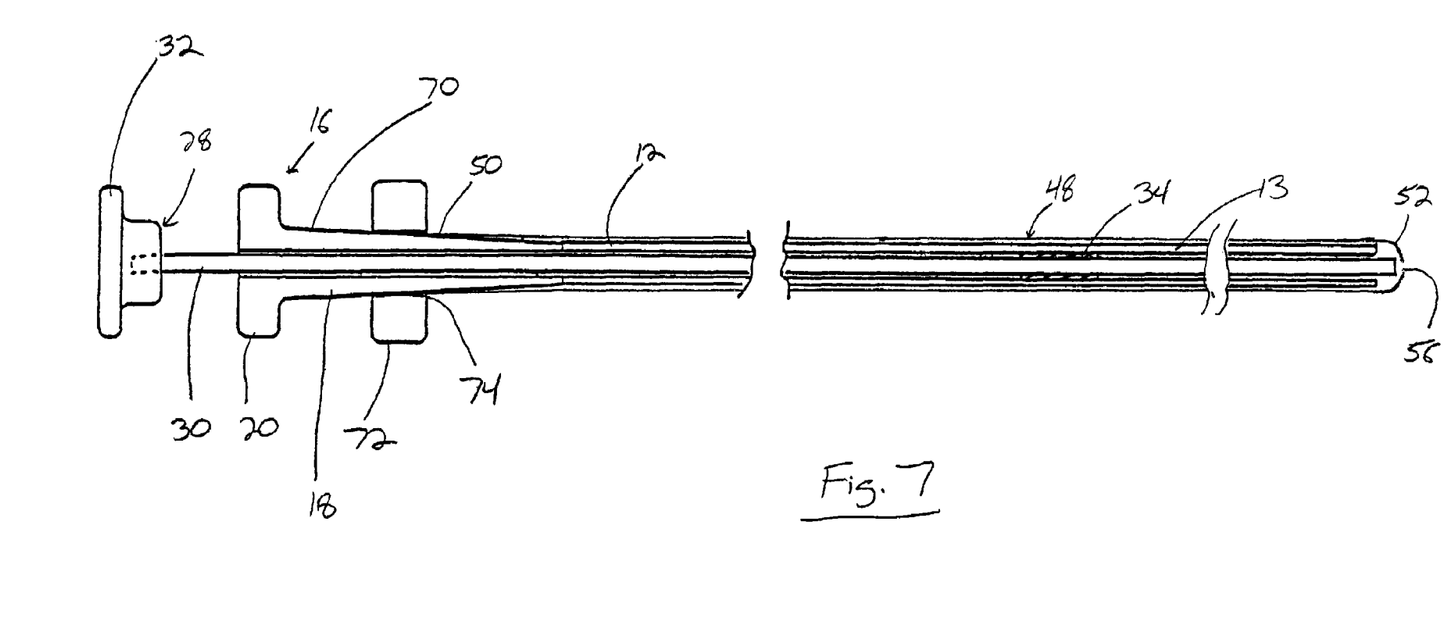
FIG. 7 is cross-sectional view of a second embodiment of the present invention.

Further, the straw 36 is maintained in engagement with the insert 58 by the engagement of the straw 36 with the guide member 34 disposed within the tubular body 12. The sheath 48 can also be used without the insert 58 to secure the straw 36 within the tubular body 12, against the guide member 34, as shown in FIG. 7.

When the insert 58 is positioned adjacent the injection end 52, the open end 64 of the straw 36 and the narrow opening 60 in the insert 58 are aligned with the restricted opening 56 in the injection end 52. The sheath 48 can be secured in this position about the tubular body 12 by the frictional engagement of the mounting end 50 of the sheath 48 with a helical ridge 68 disposed on the tube 18 of the head 16 (shown in FIG. 5). Alternatively, as is known in the art, as shown in FIG. 7, the tube 18 can be formed to have a sloped side wall 70 that flares outwardly from the tubular body 12 to the flange 20, thereby increasing the diameter of the tube 18 from the body 12 to the flange 20. To assist the positioning of the sheath 48 around the body 12 and this configuration for the head 16, the mounting end 50 can also be cut to form a slit (not shown) that extends generally parallel to the axis of the sheath 48 to enable the mounting end 50 to expand as the body 12 is inserted. Thus, the mounting end 50 of the sheath 48 splits along the cut in the sheath 48 to accommodate the increase in diameter of the tube 18 as the mounting end 50 is pushed along the tube 18. When the mounting end 50 has been slid upwardly along the sloped side wall 70 of the tube 18 a sufficient distance, a fastening structure such as a mounting O-ring 72 having a central opening 74 can be placed around the sheath 48 at the injection end 52 and slid upwardly along the sheath 48 towards the mounting end 50 to frictionally engage the mounting end 50 of the sheath 48 between the O-ring 72 and the head 16. The sloped side wall 70 of the tube 18 can also be serrated, grooved or ridged to form a gripping surface 78 that enhances the engagement of the sheath 48 between the sloped side wall 70 of the tube 18 and the O-ring 72. Preferably, the gripping surface 78 includes a spiral ridge that engages the sheath 48 and O-ring 72. The engagement of the sheath 48 around the tube 18 can also be enhanced by roughening the material forming the sheath 48 or otherwise deforming the end of the sheath 48 positioned around the tube 18, such as by adding a spiral groove (not shown) complementary to the mounting end 50 of the sheath 48.

Once the sheath 48 is secured around the tubular body 12, the rod 30 of the plunger 28 can be inserted through the head 16 into the passage 14. By pressing the handle 32 of the plunger 28 towards the head 16, the rod 30 passes through the guide member 34 and into closed end 65 of the straw 36. As the plunger 28 is pressed towards the head 16, the rod 30 contacts the plug 66 within the closed end 65, pressing the plug 66 along the length of the straw 36 and ejecting the material contained within the straw 36 outwardly from the tubular body 12 through the restricted opening 56 in the sheath 48. After the material has been expelled from the straw 36, the plunger 28 is withdrawn from the body 12 such that the sheath 48 and straw 36 can be removed from the tubular body 12 and discarded, allowing another straw 36 and sheath 48 to be mounted to the syringe 10 for a successive use of the syringe 10.

All the disclosed embodiments are useful in conjunction with devices such as are used for the purpose of inserting medicinal material into an animal, or fluids for the purpose of artificial impregnation, or the like. As such, there are virtually innumerable uses for the present invention, all of which need not be detailed here. All the disclosed embodiments can be practiced without undue experimentation.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. For example, although plastic or metal is preferred for the device and its various components, any similarly suitable any material could be used. Also, it is possible to use the inventive device without a sheath, insert, etc.

Moreover, the individual components need not be formed in the disclosed shapes, or assembled in the disclosed configuration, but could be provided in virtually any shape, and assembled in virtually any configuration. Further, although for instance the plunger, the chamber, and/or the sheath are described herein as physically separate modules, it will be manifest that such elements may be partially or fully integrated components of the device. Finally, it is conceivable that all the disclosed features of each disclosed embodiment can be combined with, or substituted for, the disclosed features of every other disclosed embodiment except where such features are mutually exclusive.

Various alternatives are contemplated as being within the scope of the following claims which particularly point out and distinctly claiming the subject matter regarded as the invention.

I claim:

1. A syringe assembly for artificially impregnating animals, the syringe assembly comprising:
   a) a tubular body defining an axial passage through the body and having a first end and a second end, the tubular body removably housing a straw containing sperm;
   b) a plunger insertable into the body; and
   c) a guide member disposed within the axial passage of the body, the guide member including a stop at one end and a recess extending inwardly from the stop terminating in an annular shoulder;
   wherein during a first use, the stop engages with a first diameter straw containing sperm; and during a second use, the annular shoulder engages with a second diameter straw containing sperm.

2. The syringe of claim 1 wherein the guide member is fixedly attached to the body.

3. The syringe of claim 1 wherein the guide member has an overall length shorter than the body.

4. The syringe of claim 1 wherein the guide member is formed of a generally rigid material.

5. The syringe of claim 4 wherein the guide member is formed of a metal; and the tubular body is formed of stainless steel and is capable of receiving a plastic sheath.

6. The syringe of claim 5 wherein the guide member is fixed to an inner wall of the tubular body.

7. The syringe of claim 6 wherein the guide member includes a guide end having a tapering guide surface opposite the stop that contacts and aligns the plunger with the axial throughbore when the plunger is pushed toward a straw.

8. The syringe of claim 1 wherein the guide member has a cross-section approximately equal to the cross-section of the axial passage.

9. The syringe of claim 8 wherein the guide member has a circular cross-section.

10. The syringe of claim 1, wherein the stop is formed by an increase in the interior thickness of the guide member from the throughbore to the one end.

11. The syringe of claim 1, wherein the stop defines a bore having a continuously decreasing diameter and the throughbore defines a generally constant diameter along the entirety of the length thereof.

12. The syringe of claim 1, wherein the stop is formed with a frustoconical surface having a gradually increasing thickness from the throughbore to the one end.

13. The syringe of claim 1 further comprising a head at the first end of the tubular body, the head including a top portion having a diverging, gripping surface for frictionally engaging a sheath positionable around the tubular body.

14. The syringe of claim 1, wherein the plunger is constructed of spring tempered stainless steel to allow for a bend near a handle to prevent the plunger from falling out when the syringe is inverted.

15. The syringe of claim 1, wherein the stop includes a flat end portion at the one end for stopping the first diameter straw; the guide member further comprising an annular shoulder for stopping the second diameter straw; wherein the recess extends inwardly from the stop to the shoulder; and wherein the tubular body is formed of stainless steel, is capable of receiving a plastic sheath and further comprises a head at the first end of the tubular body, the head including a top portion having a diverging, gripping surface for frictionally engaging a sheath positionable around the tubular body.

16. The syringe of claim 1, wherein the plunger includes identifying indicia created by a laser.

17. The syringe of claim 16, wherein the indicia is specific to the owner of the device.

18. An assembly for artificially inseminating an animal comprising:
   a) a stainless steel syringe assembly including a tubular body having a head with an axial aperture, the head fixedly attached at one end, an open end opposite the head, the body defining an axial passage therethrough, a guide member fixed within the axial passage and spaced from the head and the open end, the guide member including a stop located opposite the head, a recess extending inwardly into the guide member from the stop, a tapered end opposite the stop and an axial throughbore communicating with the recess and the tapered end, and a stainless steel plunger including an elongate rod having a handle at one end, the rod inserted through the tubular body and the throughbore in the guide member; and
   b) an elongate straw containing sperm and having first and second ends, the first end proximate the tubular body head and the second end proximate the tubular body open end; and having a plug formed of a deformable material adjacent the first straw end and proximate the tubular body head, and an open end opposite the plug at the second straw end, distal the tubular body head.

19. The assembly of claim 18 wherein the straw is a larger diameter straw and the guide member engages the straw with the stop.

20. The assembly of claim 18 wherein the straw is a small diameter straw and the guide member engages the straw with the recess of the guide member.

21. The assembly of claim 18 wherein the guide member includes an annular shoulder forming an inner end of the recess opposite the stop.

22. The assembly of claim 18 further comprising: a disposable sheath for positioning around the body, the sheath having a mounting end and a restricted end and a straw engaging member disposed within the sheath between the mounting end and the restricted end.

* * * * *